(12) United States Patent
Watson

(10) Patent No.: US 7,575,590 B2
(45) Date of Patent: Aug. 18, 2009

(54) BRANCH VESSEL GRAFT DESIGN AND DEPLOYMENT METHOD

(75) Inventor: James R. Watson, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 11/928,535

(22) Filed: Oct. 30, 2007

(65) Prior Publication Data
US 2008/0058918 A1  Mar. 6, 2008

Related U.S. Application Data

(62) Division of application No. 11/035,230, filed on Jan. 13, 2005, now Pat. No. 7,306,623.

(51) Int. Cl.
*A61F 2/06* (2006.01)
(52) U.S. Cl. ............... 623/1.12; 623/1.11; 623/1.23
(58) Field of Classification Search ............. 623/1.11, 623/1.12, 1.44, 1.23, 1.16, 1.13
See application file for complete search history.

(56) References Cited

U.S. PATENT DOCUMENTS

| | | | |
|---|---|---|---|
| 4,313,231 A | 2/1982 | Koyamada | |
| 4,728,328 A | 3/1988 | Hughes | |
| 5,123,917 A | 6/1992 | Lee | |
| 5,151,105 A | 9/1992 | Kwan-Gett | |
| 5,306,294 A * | 4/1994 | Winston et al. | 623/1.11 |
| 5,522,881 A * | 6/1996 | Lentz | 623/1.13 |
| 5,591,195 A * | 1/1997 | Taheri et al. | 623/1.11 |
| 5,693,085 A * | 12/1997 | Buirge et al. | 623/1.13 |
| 5,709,713 A | 1/1998 | Evans et al. | |
| 5,807,398 A * | 9/1998 | Shaknovich | 623/1.11 |
| 5,833,694 A * | 11/1998 | Poncet | 623/1.11 |
| 5,843,166 A | 12/1998 | Lentz et al. | |
| 5,876,448 A * | 3/1999 | Thompson et al. | 623/1.13 |
| 5,984,955 A | 11/1999 | Wisselink | |
| 6,030,414 A | 2/2000 | Taheri | |
| 6,059,824 A | 5/2000 | Taheri | |
| 6,099,548 A | 8/2000 | Taheri | |
| 6,193,745 B1 * | 2/2001 | Fogarty et al. | 623/1.12 |
| 6,241,764 B1 | 6/2001 | Villafana | |
| 6,334,867 B1 | 1/2002 | Anson | |
| 6,395,018 B1 | 5/2002 | Castaneda | |

(Continued)

*Primary Examiner*—Corrine McDermott
*Assistant Examiner*—Cheryl Miller

(57) ABSTRACT

A branch graft stent system includes a tubular primary graft having a branch graft opening which when deployed is located in alignment with a side branch vessel emanating from the primary vessel in which a branch graft is deployed. A connector (flange) member forms a perimeter of the branch graft opening and is constructed so that the connector member is substantially flush with the wall of the tubular primary graft. The tubular branch graft has a first expandable ring and a second expandable ring spaced apart from each other as part of a connection section located at a proximal end of the tubular branch graft. The first expandable ring, the second expandable ring, and graft or other material spaced between the first expandable ring and the second expandable ring when engaged with the perimeter of the branch graft opening of the primary graft, the assembly forms a flexible sealed connection between the primary graft and branch graft lumens to continue to exclude the aneurysm while providing a conduit for blood flow to the branch vessel. A distal end of the branch graft can be anchored by a balloon expandable or a self-expanding stent to the wall of the branch vessel beyond the aneurysm.

20 Claims, 14 Drawing Sheets

U.S. PATENT DOCUMENTS

| | | |
|---|---|---|
| 6,451,048 B1 | 9/2002 | Berg et al. |
| 6,585,762 B1 | 7/2003 | Stanish |
| 6,652,567 B1 | 11/2003 | Deaton |
| 6,719,768 B1 | 4/2004 | Cole et al. |
| 6,827,726 B2 | 12/2004 | Parodi |
| 6,827,736 B2 | 12/2004 | Perouse |
| 6,989,024 B2 * | 1/2006 | Hebert et al. .............. 623/1.11 |
| 6,994,722 B2 | 2/2006 | DiCarlo |
| 2002/0198585 A1 | 12/2002 | Wisselink |
| 2003/0033005 A1 | 2/2003 | Houser et al. |
| 2003/0093145 A1 | 5/2003 | Lawrence-Brown et al. |
| 2004/0117003 A1 | 6/2004 | Ouriel et al. |
| 2004/0243221 A1 | 12/2004 | Fawzi et al. |
| 2005/0222667 A1 * | 10/2005 | Hunt ......................... 623/1.13 |
| 2005/0228484 A1 | 10/2005 | Stephens et al. |
| 2005/0273154 A1 | 12/2005 | Colone |
| 2006/0095114 A1 | 5/2006 | Hartley et al. |
| 2006/0149360 A1 | 7/2006 | Schwammenthal et al. |
| 2007/0106365 A1 * | 5/2007 | Andreas et al. ............ 623/1.11 |
| 2007/0179592 A1 | 8/2007 | Schaeffer |

* cited by examiner

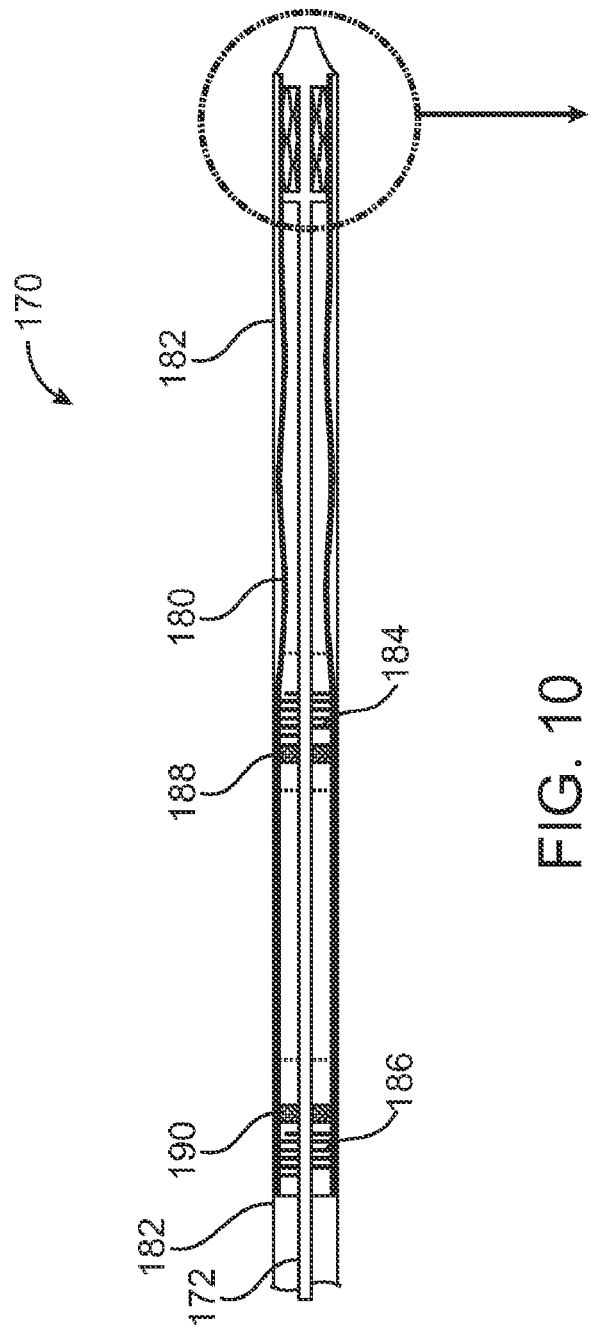
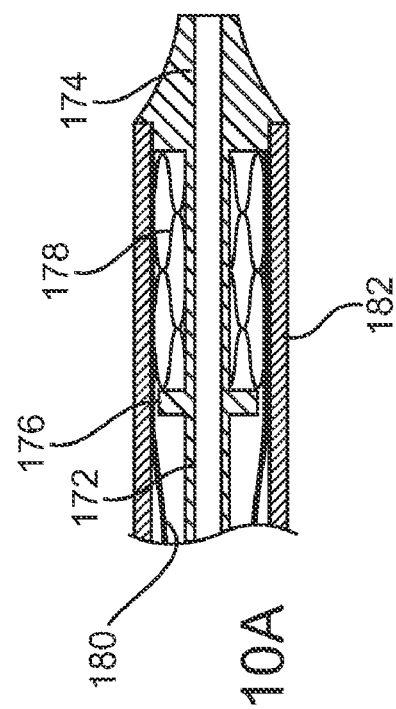
FIG. 10
FIG. 10A

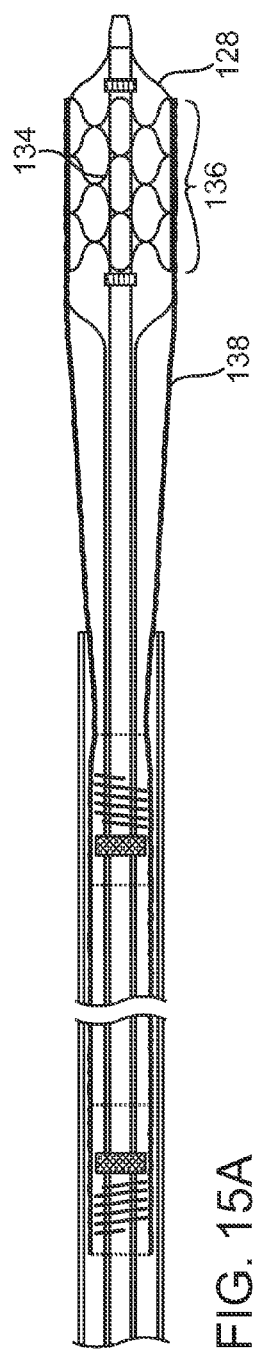
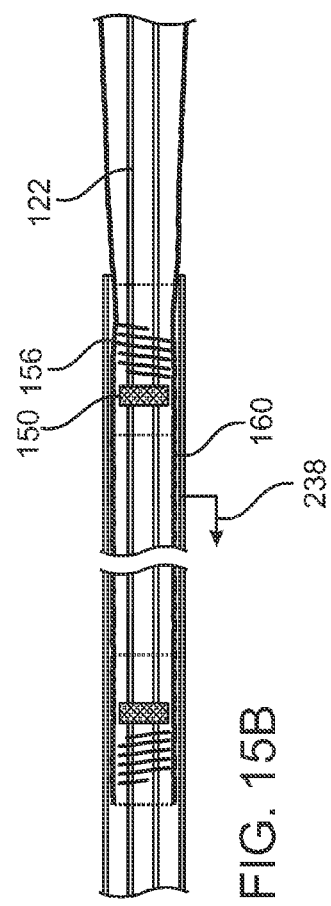
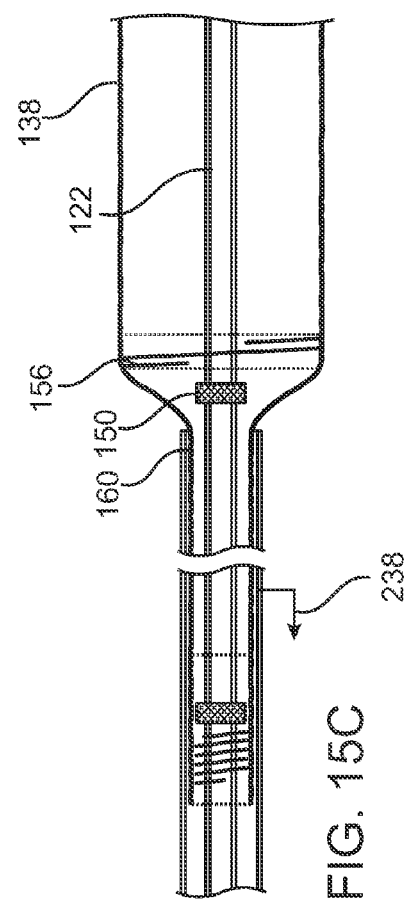
FIG. 15A
FIG. 15B
FIG. 15C

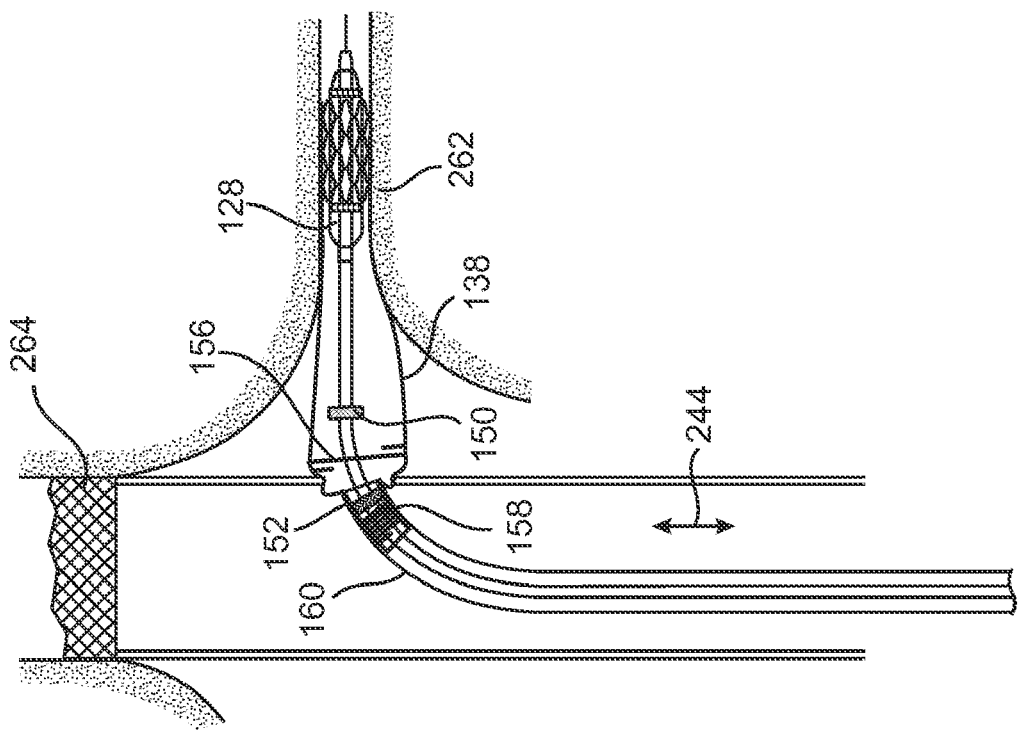
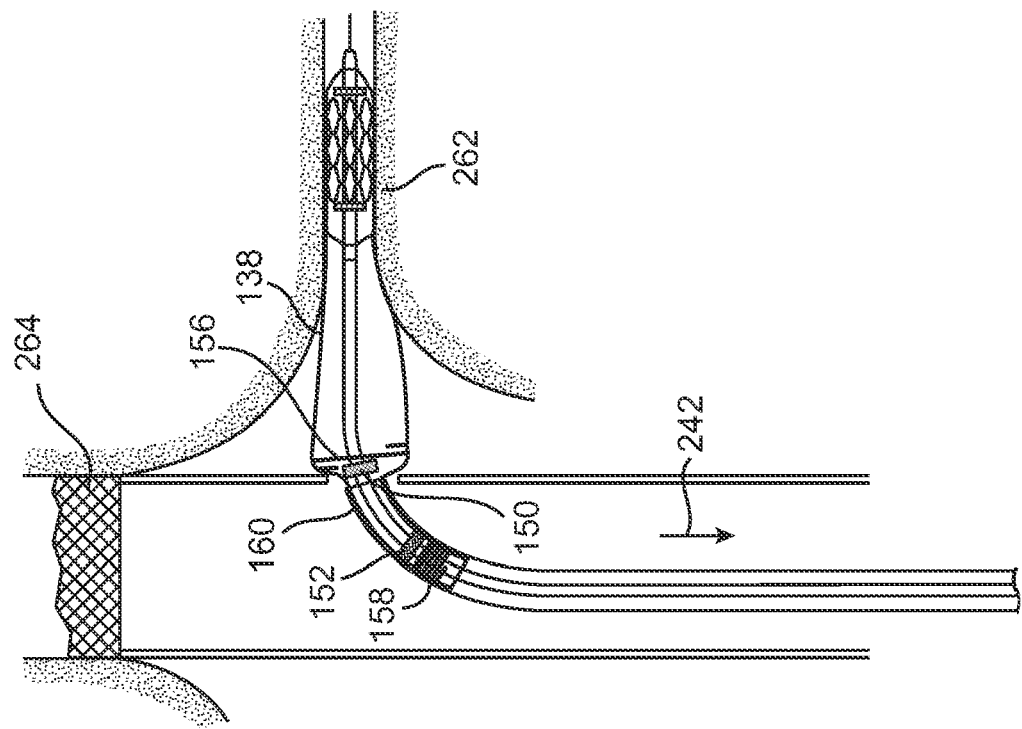

BRANCH VESSEL GRAFT DESIGN AND DEPLOYMENT METHOD

This application is a divisional of U.S. patent application Ser. No. 11/035,230, filed on Jan. 13, 2005, now U.S. Pat. No. 7,306,623 entitled "BRANCH VESSEL GRAFT DESIGN AND DEPLOYMENT METHOD", which is herein incorporated by reference in its entirety.

FIELD OF THE INVENTION

This invention relates generally to endoluminal medical devices and procedures, and more particularly to branch vessel grafts secondarily attached to a main vessel stent graft using a system of rings coupled to the branch graft for a sealed branch vessel graft connection to a main stent graft.

BACKGROUND OF THE INVENTION

Prostheses for implantation in blood vessels or other similar organs of the living body are, in general, well known in the medical art. For example, prosthetic vascular grafts formed of biocompatible materials (e.g., Dacron or expanded, porous polytetrafluoroethylene (PTFE) tubing) have been employed to replace or bypass damaged or occluded natural blood vessels. A graft material supported by framework is known as a stent graft. In general, the use of stent grafts for treatment or isolation of vascular aneurysms and vessel walls which have been thinned or thickened by disease (endoluminal repair or exclusion) are well known. Many stent grafts, are "self-expanding", i.e., inserted into the vascular system in a compressed or contracted state, and permitted to expand upon removal of a restraint. Self-expanding stent grafts typically employ a wire or tube configured (e.g. bent or cut) to provide an outward radial force and employ a suitable elastic material such as stainless steel or Nitinol (nickel-titanium). Nitinol may additionally employ shape memory properties. The self-expanding stent graft is typically configured in a tubular shape of a slightly greater diameter than the diameter of the blood vessel in which the stent graft is intended to be used. In general, rather than performing an open surgical procedure which is traumatic and invasive to implant a bypass graft, stents and stent grafts are preferably deployed through a less invasive intraluminal delivery, i.e., cutting through the skin to access a lumen or vasculature or percutaneously via successive dilatation, at a convenient (and less traumatic) entry point, and routing the stent graft through the vascular lumen to the site where the prosthesis is to be deployed.

Intraluminal deployment is typically effected using a delivery catheter with a coaxial inner (plunger member) and an outer (sheath) tubes arranged for relative axial movement. The stent (or stent graft) is compressed and disposed within the distal end of an outer catheter tube in front of a stent stop fixed to the inner member. The catheter is then maneuvered, typically routed though a lumen (e.g., vessel), until the end of the catheter (and the stent graft) is positioned at the intended treatment site. The stent stop on the inner member is then held stationary while the sheath of the delivery catheter is withdrawn. The inner member prevents the stent graft from being withdrawn with the sheath. As the sheath is withdrawn, the stent graft is released from the confines of the sheath and radially expands so that at least a portion of it is in substantially conforming surface contact with a portion of the surrounding interior of the lumen e.g., blood vessel wall or anatomical conduit. As a convention used to describe the ends of devices implanted in the arterial system the proximal end of the stent graft is the end closest to the heart as taken along the path of blood flow from the heart, whereas the distal end is the end furthest away from the heart once deployed. An example of stent graft positioning and deployment is shown in FIG. 1, which is a FIGURE taken from U.S. Pat. No. 5,591,195 to Taheri et al.

FIG. 1 shows an aneurysm 30 in a vascular artery 32 (such as an aorta). A stent graft 34 spanning the aneurysmal sac 36 is show as just having been deployed from a delivery system 38. The stent graft 34 is constructed of a tubular graft (textile or cloth) material 40 which at each tubular end is radially expanded by zig zag type (Z-type) tubular stents 42, 44. A connecting bar 46 (shown in dashed lines) connects the two end stents 42, 44. The stent graft 34 deployed at the location of the aneurysm 30 creates a separate isolated flow path for blood through the lumen of the stent graft 34 such that the aneurysmal sac 36 of the aneurysm 30 is excluded and is no longer subject to the normal maximum blood pressure experienced in the vascular arterial system at the location of the aneurysm 30. Depending on the construction of the graft material 40 it may either seal immediately or provide a very slight permeable leakage (blush) which through the biological activity in the blood stream will cause the graft material 42 to be tightly sealed over time.

Stent grafts can also be used in patients diagnosed with aneurysms close to or crossing branch openings to renal arteries or other branch arteries (e.g., celiac, suprarenal, interior mesenteric). Stent graft designs with side openings are designed for use in regions of the aorta from which side branches feed blood to organs like the kidney, spleen, liver, and stomach. FIGS. 2 and 3 show examples from U.S. Pat. No. 6,030,414 to Taheri, as described therein. Such endovascular grafts have been designed for use where the proximal end of the graft is securely anchored in place, and fenestrations are configured and deployed to avoid blocking or restricting blood flow into the renal arteries. The endovascular graft must be designed, implanted, and maintain position in a manner which does not impair the flow of blood into the branch arteries.

Stent grafts 50, 60 with side openings or fenestrations 52, 54, 62, 64 are shown in FIGS. 2 and 3. Such fenestrations 52, 54, 62, 64 do not form discrete conduit(s) through which blood is channeled into each branch artery 51, 53, 61, 63, 67, 69. As a result, the edges of the graft surrounding the fenestrations 52, 54, 62, 64 could be prone to: i) the leakage of blood into the space between the outer surface 56, 66 of the aortic graft (stent graft 50,60) and the surrounding aortic wall 55, 65; or ii) post-implantation migration or movement of the stent graft 50, 60 causing misalignment of the fenestration(s) 52, 54, 62, 64 and the branch artery(ies) 51, 53, 61, 63, 67, 69—with resultant impairment of flow into the branch artery (ies).

FIG. 4 shows an alternate prior art configuration for a stent graft 70 having integrally constructed tubular branch members 71, 72, 73, 74, where the branch tubular members are placed into position using a series of guidewires 76, 77, 78, 79, where the top (proximal) end 80 fixed by a separately delivered stent (not shown) above the aneurysmal part of the aorta. A full explanation of the mechanism for delivery and final fixation of the stent graft with integral branches (as shown in FIG. 4) can be had by reference to U.S. Pat. No. 6,099,548 to Taheri the disclosure of which is incorporated herein by reference.

FIGS. 5 and 6 show an alternate arrangement for construction of a branch vessel connection. FIGS. 5 and 6 are examples taken from U.S. Pat. No. 6,059,824 to Taheri, incorporated herein by reference. In FIG. 5 the main stent body 90 once properly positioned in the main artery (not shown) has an opening wide annular land portion collar 93 aligned with side branching collateral arteries (not shown). The wide annular land portion collar 93 includes a series of inlets (or indentations) 94a, 94b. A collateral cylindrical stent body 92 is mated to the main stent body 90 through an annular land portion flange located at the proximal end of the collateral cylindrical body 92. The annular land portion collar 95 includes several detents 96a, 96b which are sized and spaced about the annular extent of the collateral collar 95 to position, hold and lock the collateral stent cylindrical body 92 mated to the main stent body 90. The detents, e.g. 96a, 96b, are received in the inlets e.g. 94a, 94b, of the main stent collar 93. An engagement balloon (not shown) located in the aorta is used to provide the force needed to lock the detents, e.g., 96a, 96b, and the inlets e.g., 94a, 94b, together.

FIGS. 7 and 8 show another prior art arrangement of a branch vessel connection to a stent graft. These FIGURES are similar to those in U.S. Pat. No. 5,984,955 to Wisselink, incorporated herein by reference. Referring now to FIGS. 7 and 8 together, a primary graft 100 includes a ring member 104 surrounding a side branch orifice 106 having a frusto-conical member 102 extending from the graft 100. A side branch orifice 106 is aligned with the location of a branch artery (as seen in FIG. 8) and then a branch graft 110 is brought in through the main graft and snapped into position as the small ring member 114 and large ring member 116 at the ends of the tapered proximal portion 112 of the branch graft 110 are pushed into interfering engagement with the frusto-conical member 102.

These examples of prior art devices to facilitate flow from an aneurysmal portion of the aorta into branch vessels show the complexity and space/volume requirements needed in the delivery system to deliver and accurately align such prior art systems. The use of fenestrations or openings in a tubular graft requires that a perimeter opening be sealed against the vascular wall to prevent the blood from passing through the tubular graft from continuing to pressurize and enlarge the surrounding aneurysmal sac. Such a main graft body can be provided with a flange or other fitting which is hard to compress to insert into a delivery catheter for deployment. And once the main stent graft body is in position then branch members need to be positioned with great care to provide a blood tight seal between the main graft body and the branch graft.

Thus, a need exists for a method and deployment system that simplifies alignment and reduces deployment forces needed to make a fluid tight connection between a main stent graft and a branch graft connected to a sidewall thereof. Ideally, such a branch graft is a part of a graft system that can treat aortic aneurysms at a location close to or at the location of a smaller vessel branching from the main vessel using a branch that makes a fluid tight connection to a port of the main graft.

Progress in this field looks to the development of new endovascular grafting systems and methods which a) may be useable for endovascular grafting in regions of a blood vessel (e.g., aorta) from which branch blood vessels (e.g., carotid, innominate, subclavian, intercostal, superior mesenteric, celiac, renal or iliac arteries) extend, and/or b) may enable more aortic aneurysm patients to be considered as candidates for endovascular repair, and/or c) may otherwise advance the state of the art of endovascular grafting to improve patient outcomes or lessen complications.

SUMMARY OF THE INVENTION

A branch graft design according to the present invention provides an improvement in locating and connecting a stent graft to a branch vessel at the location of an aneurysm in the main vessel. A branch graft design includes a tubular branch graft having a proximal end and a distal end and a lumen extending along the tubular branch graft axis longitudinally therethrough. A first self-expanding support ring is coupled to a first annular ring receiving section encircling the tubular branch graft at its proximal end. A second self-expanding support ring is coupled to a second annular ring receiving section circumferentially encircling the tubular branch graft at its proximal end. The second annular ring receiving section is disposed proximally parallel to and a ring receiving section separation length along the branch graft axis from the first annular ring receiving section such that the second annular receiving section is located closer to the distal end of the graft than the first annular ring receiving section. A tubular main graft constructed of a main graft material has a side opening having a perimeter with a substantially flush reinforcing ring or flange. The ring receiving section separation portion of the branch graft material engages the perimeter of the side opening to form a seal between the main graft and the branch graft when the first self expanding support ring which is coupled to the first annular ring receiving section circumferentially encircling the branch graft at the proximal end is disposed inside the side opening of the main graft and the second self expanding support ring which is coupled to the second annular ring receiving section circumferentially encircling the branch graft at the proximal end is disposed outside the side opening of the branch graft. The support rings may be made of nitinol and configured in a multiple winding hoop or a stent configuration and the support rings can be sewn to the inside or outside of tubular branch graft. The ring receiving separation portion of the branch graft may be made from the same material as the tubular branch graft or of a semi-rigid (still pliable) material different from the material forming the tubular branch graft.

An embodiment according to the invention further includes a method for deployment of a main stent graft and branch vessel graft comprising the steps of at least partially deploying the main stent graft and aligning a substantially flush branch vessel port of the main stent graft with a branch vessel: deploying the branch vessel graft into the substantially flush branch vessel port wherein that the branch vessel graft is engaged with the substantially flush branch vessel port of the main stent graft by exposing a first ring integral to the branch vessel graft to a first side of the branch vessel port and subsequentially exposing a second ring integral to the branch vessel graft on an opposing side of the branch vessel port.

The embodiment according to the invention can be further described to include a branch graft delivery system comprising a branch graft disposed on a delivery catheter having a sheath surrounding a seal portion of the branch graft. The seal portion of the branch graft includes a first annular self expanding ring section and a second annular self expanding ring section. The ring sections are circumferentially coupled to the graft at first and second locations, respectively, wherein the first and second locations are spaced from each by a cylindrical channel seal forming section. An inner member of the delivery catheter includes a first stop and a second stop each of which extend laterally outward from the inner member to a diameter slightly less than the inside diameter of the delivery sheath. Annular space between the inside diameter of the sheath and the outside diameter of the inner member provides clearance for the thickness of the graft material to fit through and be carried in the annular space, while preventing the first and second annular self expanding support ring sections which are thicker because they contain or are attached to the support ring member from passing through the annular space. When the sheath is positioned to surround a first stop the first annular self expanding ring section is prevented from moving towards the second annular self expanding ring section and when the sheath is positioned to surround the second stop a second annular self expanding ring section is prevented from moving towards the first expanding ring section.

BRIEF DESCRIPTION OF THE DRAWINGS

FIGS. 10 and 10A are a schematic cross sectional diagram and a close up view of a tip of a self expanding branch graft configuration on its delivery system;

FIGS. 15A, 15B, 15C, 15D, 15E, 15F, and 15G are schematic cross sectional diagrams showing the progressive steps of deployment of a branch graft assembly;

FIGS. 16A, 16B, 16C, 16D, 16E, 16F, and 16G are schematic cross sectional views of the steps in delivery and deployment of a branch graft into a side branch vessel from an aneurysmal sac where a tubular main graft has already been placed. The steps of deployment as pictured in FIGS. 16A-16G provide in situ view of the deployment of the branch graft similar to, though not directly correlating to, the steps of branch deployment pictured in FIGS. 15A-15G described above.

DETAILED DESCRIPTION

Figure 1:
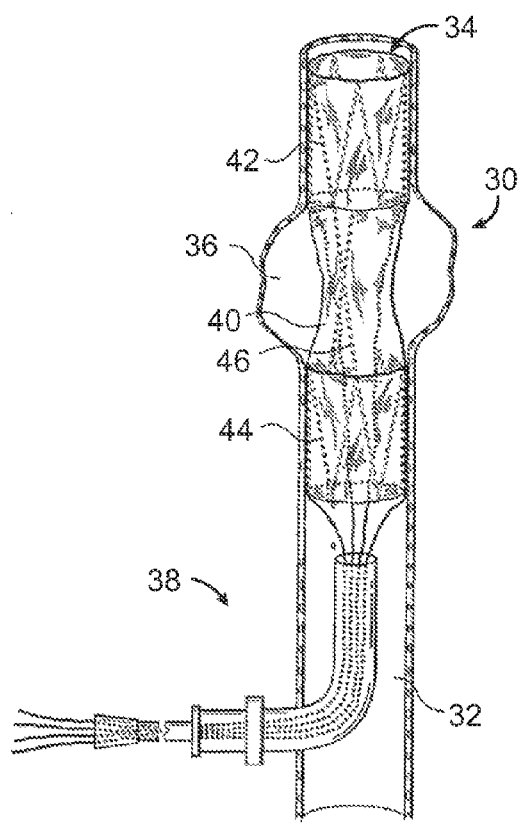
FIG. 1 is a schematic cross sectional view of a tubular stent graft of the prior art disposed across an aneurysm in an arterial vessel.
Figure 2:
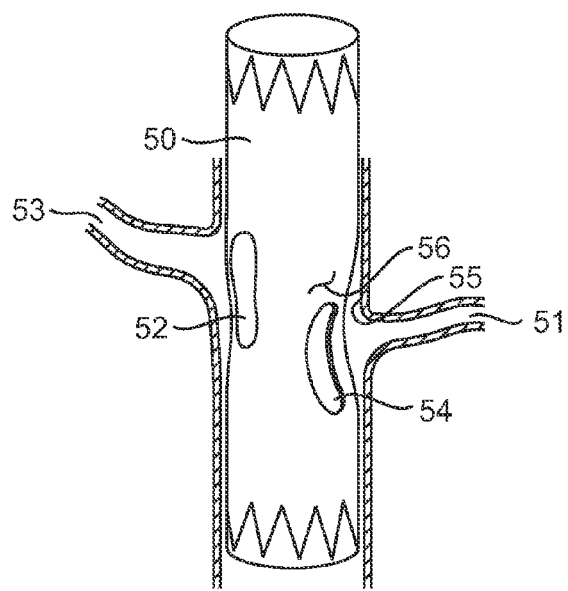
FIG. 2 is a schematic cross sectional view of a prior art stent graft having fenestrations which match side branch openings in a main arterial passage having branch vessels extending from the main vessel.
Figure 3:
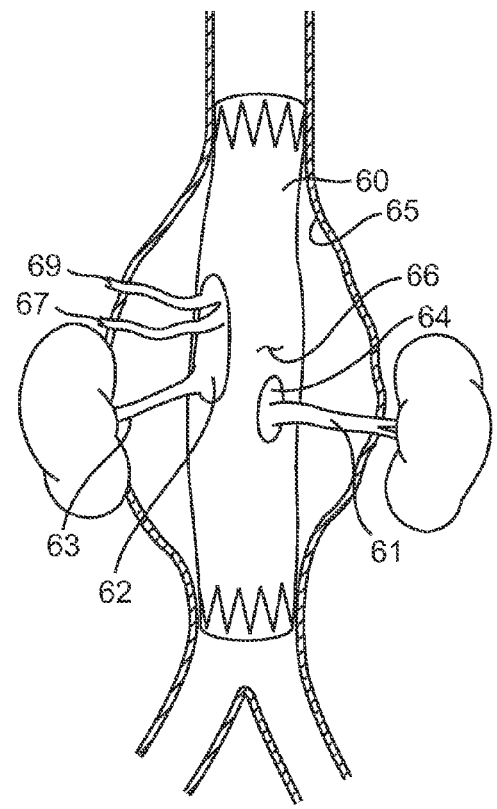
FIG. 3 is a schematic cross sectional view of a stent graft deployed across an aneurysm in an aorta, where the stent graft has fenestrations positioned at locations so that branch vessels are fed through the fenestrations.
Figure 5:
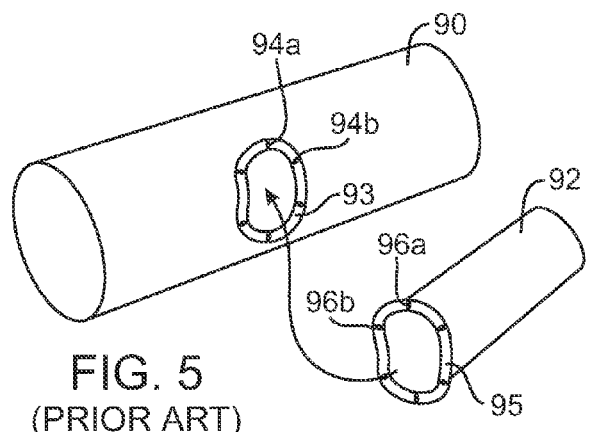
FIGS. 5 and 6 show a pre assembly and post assembly, respectively, pictorial diagram of a main stent body to which a cylindrical collateral stent body is attached in situ.
Figure 6:
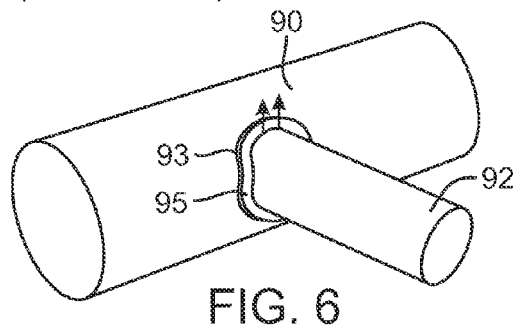
Figure 4:
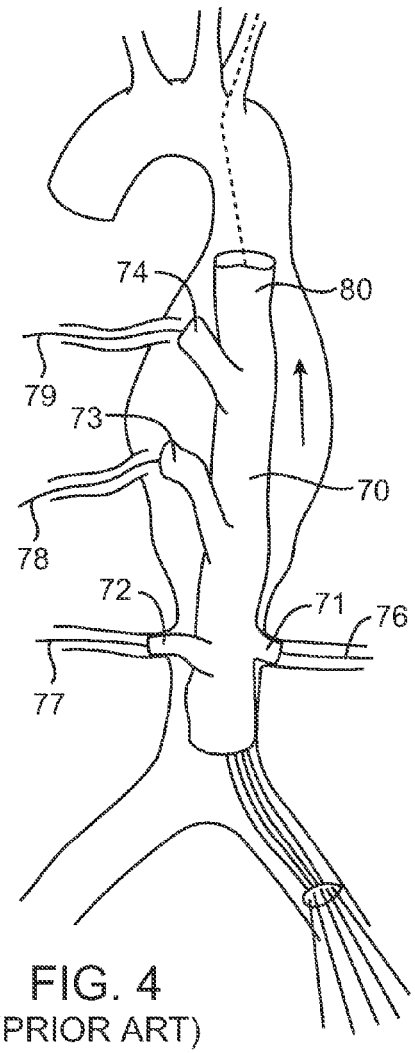
FIG. 4 is a schematic cross section showing a position of a stent graft with several integral side branch graft passages in the process of being positioned to exclude blood flow to the aortic aneurysm while providing an artificial lumen to feed the branch vessels that originate in the area of the aortic aneurysm.
Figure 8:
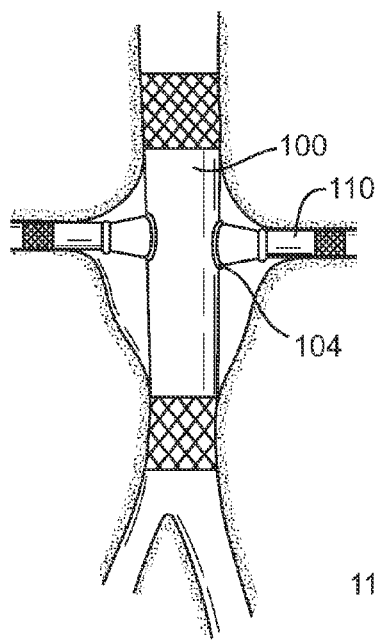
FIGS. 7A, 7B and 8 show close up and schematic cross sectional diagrams of a branch graft connection to a primary stent graft providing branching connections in an aorta where an aneurysmal sac has created a widening of the aorta at a location of branch vessels.
Figure 7:
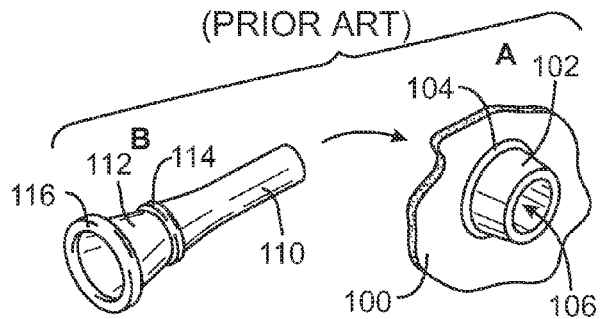
Figure 9:
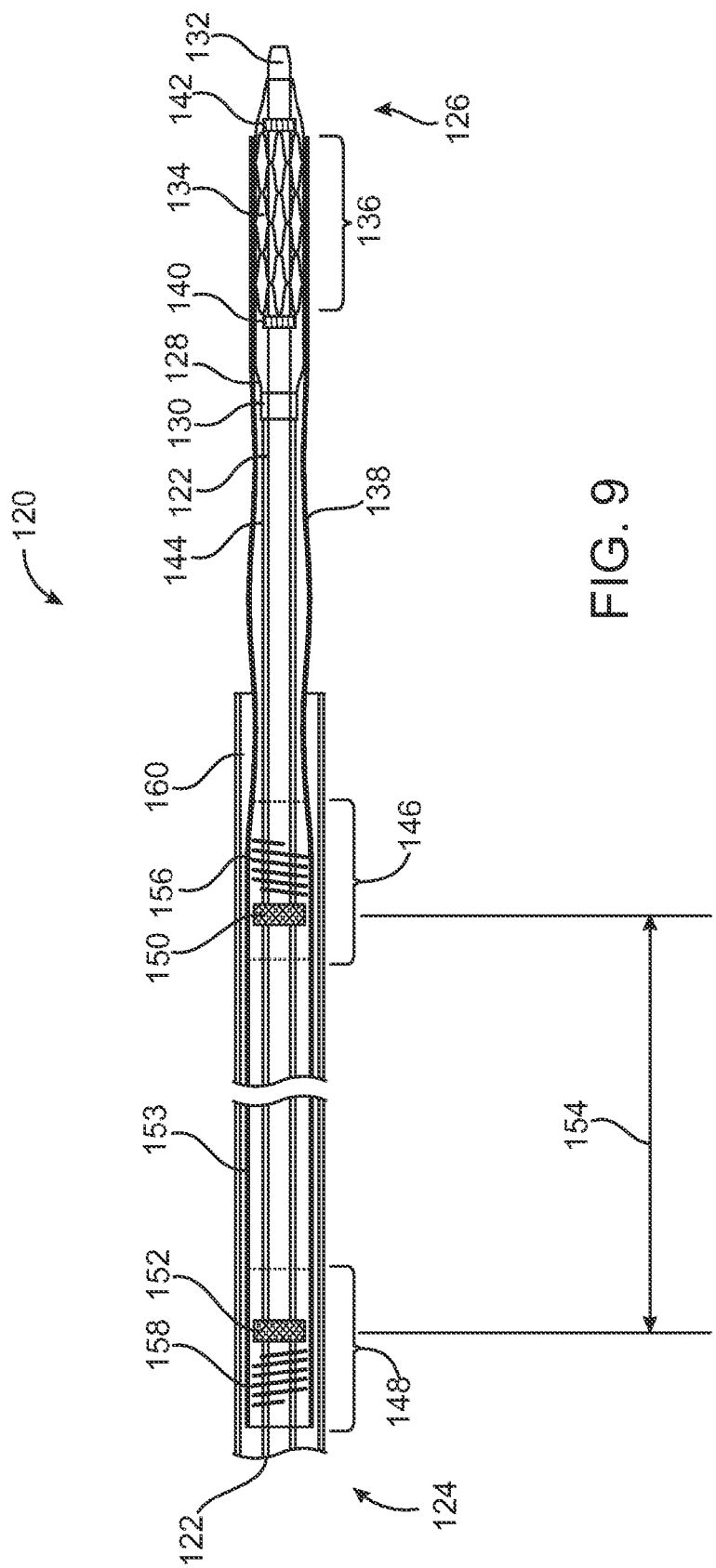
FIG. 9 is a schematic cross sectional view of a balloon expandable branch graft configuration on its delivery system.

FIG. 9 shows a balloon expandable branch graft stent system 120 in accordance with the invention. A catheter having a catheter inner member (inner tube) 122 extends from a proximal end 124 to a distal end 126 of the catheter. A balloon 128 is located at the distal end 126 of the catheter and bonded to the catheter inner member 122 in a balloon to catheter member distal bond region 132. The proximal end of the balloon 128 is bonded at a balloon to outer member proximal bond region 130 to an outer member 144 that provides a coaxial annular lumen between its inner surface and the outer surface of the catheter inner member 122. The balloon expandable stent 134 compressed around the balloon 128 is positioned between a stent location proximal marker band 140 and a stent location distal marker band 142 both mounted on the catheter inner member 122. A tubular graft material 138 is sewn or bonded to the outside of the stent in a stent to graft material bonding section 136. Tubular graft material 138 extends proximally from the stent 134 to a distal graft ring (hoop-stent) receiving section (pocket) 146 where a self expanding hoop or stent is disposed in a circumferential graft pocket containing a distal coiled nitinol hoop 156. An outer sheath 160 prevents the distal coiled nitinol hoop 156 from expanding in a radial direction while the axial limits of the distal graft ring receiving pocket 146 limits the axial movement (expansion) of the distal coiled nitinol hoop 156. Similarly the graft 138 at its proximal end contains a proximal graft ring (hoop-stent) receiving section (pocket) 148 such that the axial length of the tubular graft material 138 extends from the proximal end of the proximal graft ring pocket 148 to the distal end of the stent 134 where it is attached (sewn or bonded) to a graft material 136 in the stent to graft material bonding section 136. A proximal coiled nitinol hoop 158 is contained within the proximal graft ring hoop receiving section pocket 148. To maintain the position of the proximal graft pocket 148 with respect to the distal graft pocket 146 and to the distal end of the stent 134 a proximal ring (hoop) stop 152 and a distal ring (hoop) stop 150 are fixed to the outer member (tube) 144 at a distance between ring (hoop) stops 154 spanned by a graft material identified as a ring receiving pockets separation section (sealing section) 153. The distance between ring hoops stops 154 is dependent upon the main graft wall thickness, the branch vessel diameter, and the main graft wall opening diameter such that the specific dimension described for the distance between hoop ring stops 154 can lengthen or shorten depending on the interaction of the main graft wall thickness the branch vessel diameter and the main graft wall opening and diameter as appropriate for a particular application and branch graft diameter size. The sealing section 153 may be made of graft material or of a more rigid but still pliable material with good surface contact sealing characteristics.

FIG. 10 is a cross sectional schematic view of a self expanding branch graft stent system 170. In this system a center member 172 extends to and is fixed to a catheter tip 174. A stent cup-disc plunger 176 (FIG. 10A) is attached to the center member 172 such that a self expanding stent 178 to which a graft material 180 is attached is disposed between the stent cup plunger 176 and the catheter tip 174. A full length sheath 182 covers the full length of the center member 172 and seats in a perimeter groove on the catheter tip 174. Similar to the configuration described for the balloon expandable system above, graft material 180 contains a series of pockets to contain the distal expandable ring (hoop-stent) 184 and a similar ring pocket to contain the proximal expandable ring (hoop-stent) 186. A distal ring (hoop-stent) stop 188 and proximal ring (hoop-stent) stop 190 are fixed to the center member 172 to maintain the pre deployment distance between the distal expandable ring (hoop-stent) 184 and the proximal expandable ring (hoop-stent) 186.

Figure 11A:
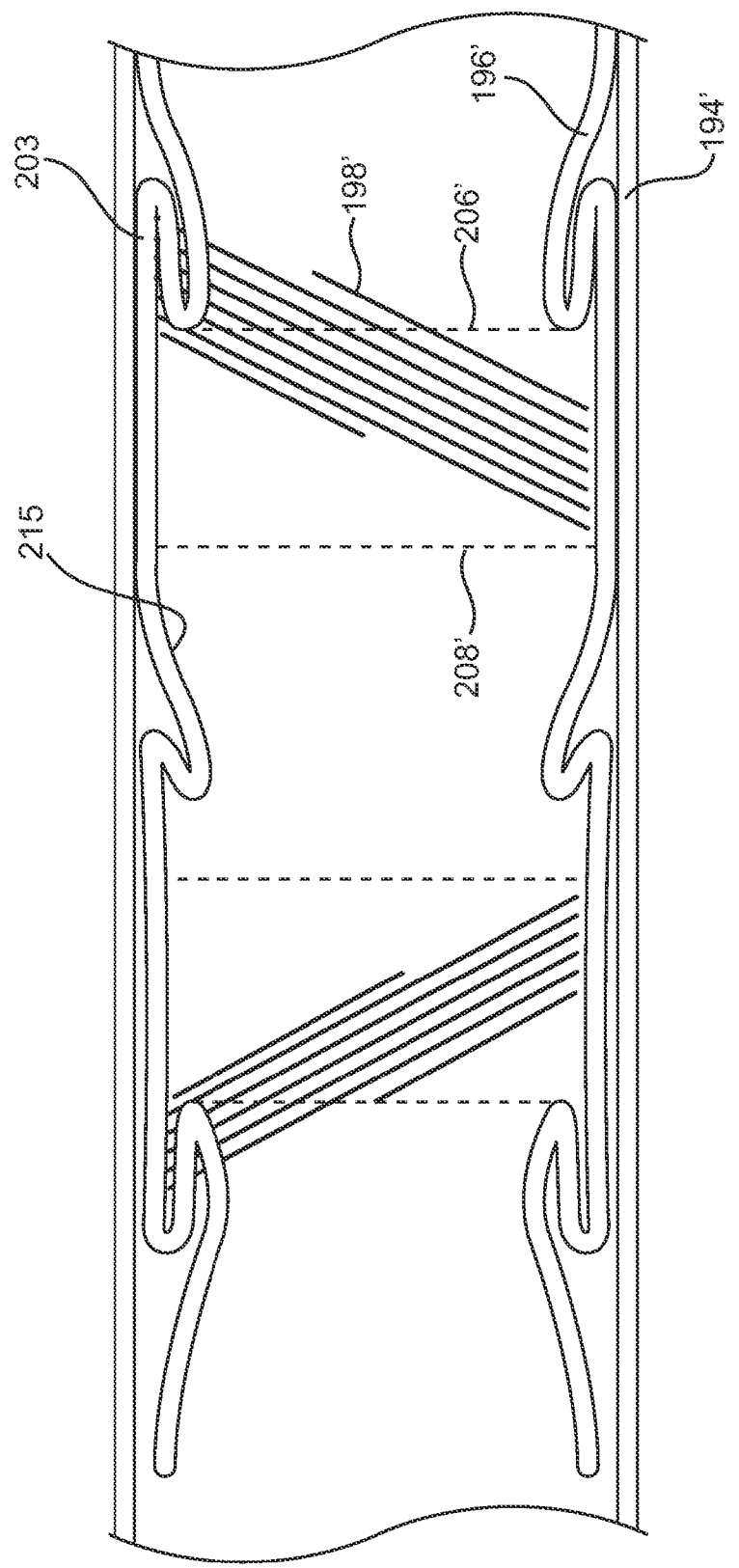
FIGS. 11 and 11A are schematic cross sectional diagrams of a set of hoop or ring like self expanding support rings in a compressed configuration.
Figure 11:
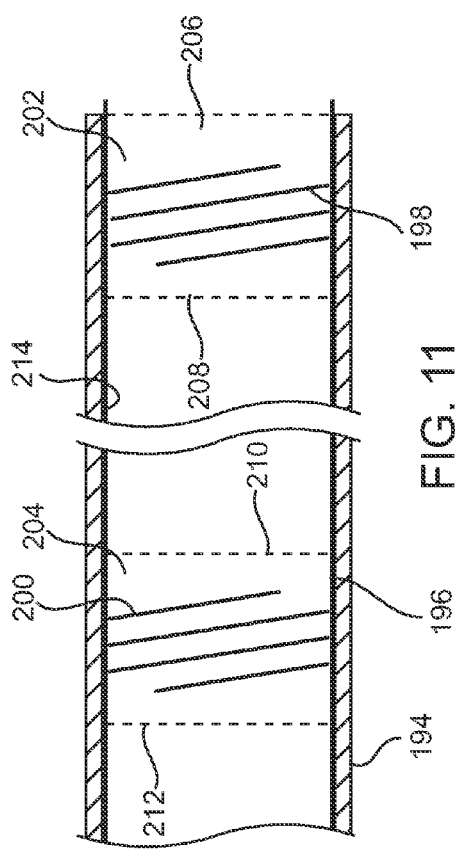

FIG. 11 is a close up of a compressed configuration of expandable hoop type ring contained in a branch graft stent system. An outer sheath 194 contains in a compressed configuration a graft material 196 which is sewn or otherwise bonded to pocket material 202 and pocket material 204, respectively. A distal ring hoop pocket seam of the distal pocket shown as a dashed line 206 is the distal limit of the distal pocket containing a compressed coiled nitinol hoop 198 while a proximal ring hoop pocket seam shown as dashed line 208 of the distal pocket connects the distal pocket material 202 to the graft material 196 to act as a closed pouch to contain the compressed coiled nitinol hoop 198. Similarly a compressed proximal coiled nitinol hoop 200 is contained within a hoop pocket (pouch) formed by proximal pocket material 204 which is bonded or sewn to the graft material 196 at coaxial circumferentially ring hoop pocket seams, i.e., distal seam of the proximal pocket 210, and proximal seam of the proximal pocket 212. A ring receiving pocket separation (seal) section 214 separates the distal seam of the proximal pocket 210 from the proximal seam of the distal pocket 208.

FIG. 11A is a close up of an alternate compressed configuration of expandable hoop type ring contained in a branch graft stent system of that shown in FIG. 11. An outer sheath 194' contains in a compressed configuration graft material 196' which is sewn or otherwise bonded to pocket of pre enlarged material 203 forming a pocket for receiving and setting the maximum diameter of expansion of a compressed coiled nitinol hoop 198'. A distal ring hoop pocket seam of the distal pocket shown as a dashed line 206' in the distal limit of the distal pocket containing a compressed coiled nitinol hoop 198' while a proximal ring hoop pocket seam shown as dashed line 208' of the distal pocket connects the distal pocket material 202 to the graft material 196' to act as a closed pouch to contain the compressed coiled nitinol hoop 198'. In this instance the graft material 196' which extends between the distal and proximal ring hoop pocket seams 206' and 208' has a bulge (disk creating) diameter which results in an annular fold of graft material that is folded over when the adjacent graft material (as shown in FIG. 11A) or tucked inside and not shown as seen or not seen in FIG. 11 such that stretching of the graft material by the expanding ring (e.g., 198') is not needed and does not take place. The angled (or tipped over) orientation of the compressed coiled nitinol hoop 198' shown in FIG. 11A, shows the position of the end of the hoop in the end of the pocket 203, as might be experienced if a fully expanded hoop in a graft material pocket were compressed to fit into a delivery sheath (e.g., 194').

Figure 12:
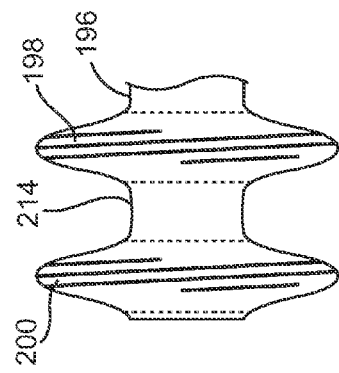
FIG. 12 is a schematic cross sectional of the support rings of the FIG. 11 in an expanded (post deployed) configuration.
Figure 13:
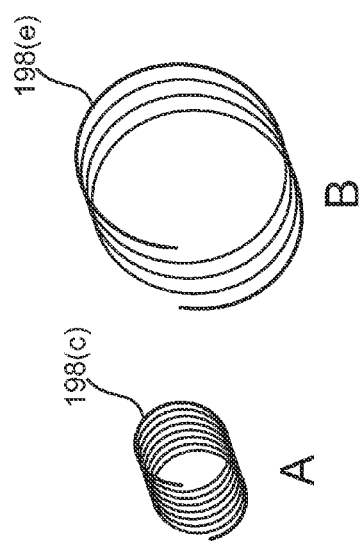
FIGS. 13A and 13B are side perspective diagrams showing a ring type self expanding support ring in a compressed (13A) and an expanded (13B) configuration as pictured in FIGS. 11 and 12, respectively.

FIG. 12 shows configuration of the coiled nitinol hoops 198, 200 in an expanded configuration. The sheath 194 shown in FIG. 11 having been retracted, the distal nitinol hoop 198 has expanded from its compressed configuration as isolated in FIG. 13A shown as 198(c) to an expanded configuration as shown in FIG. 13B identified by 198(e). The proximal coiled nitinol hoop 200 is similarly expanded so that the two expanded hoops contained within the hoop pocket spaces act as expanding discs along the length of the graft material and create an expanding or sealing area at the ring receiving pocket separation section 214 (which may be very short length and have a diameter as large as if not larger than, the main graft opening to which it is intended to seal).

Figure 14:
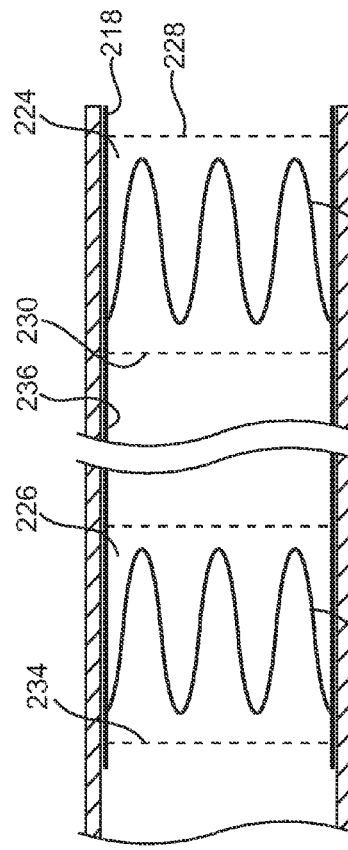
FIG. 14 is schematic cross section showing an alternate configuration of self expanding support rings where the support rings are configured from a stent of a zig zag configuration, the compressed state of the rings is shown.

FIG. 14 shows a self expanding configuration of a self expanding ring stent configuration. An outer sheath 217 contains in a compressed configuration a graft material 218 inside of which, or on the outside of which, is attached or sewn in place a set of distal (220) and proximal (222) Z-type self expanding stents. The stents can be sewn to the inside or outside of the graft material or a pocket of material or pocket (pouch) space 224, 226 can be provided in which the self expanding stents 220, 222 can expand. The pockets 224, 226 have axial limits along ring stent pocket seams 228, 230, 232, 234. The graft material 218 includes a ring receiving pocket separation (seal) section 236 between the two central pockets seam 230, 232.

One sequence for deployment of a branch graft to be sealed to an opening in a main graft will now discussed by reference to FIGS. 15A-G and 16A-G. Irrespective of whether a balloon expandable stent or a self expanding stent is used to anchor the distal end of the graft material in the branch vessel, such a stent can be used solely to anchor the graft or be used multifunctionally to anchor the graft and treat and provide a lesion opening function when there is an occlusion or narrowing in the branch vessel into which the branch graft system is being placed.

Figure 16B:
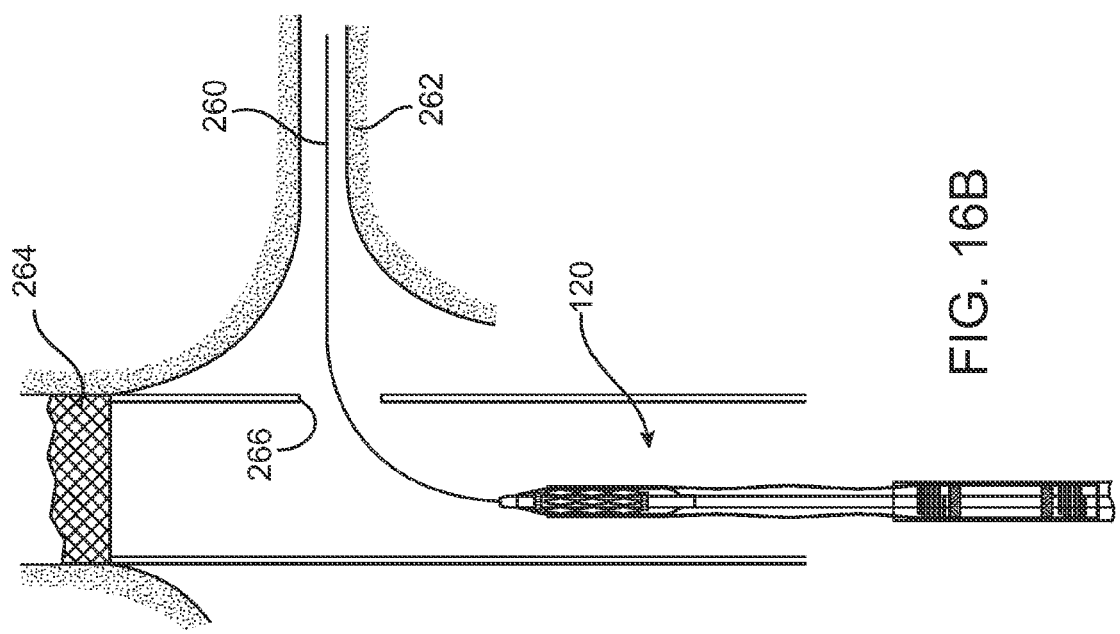
Figure 16A:
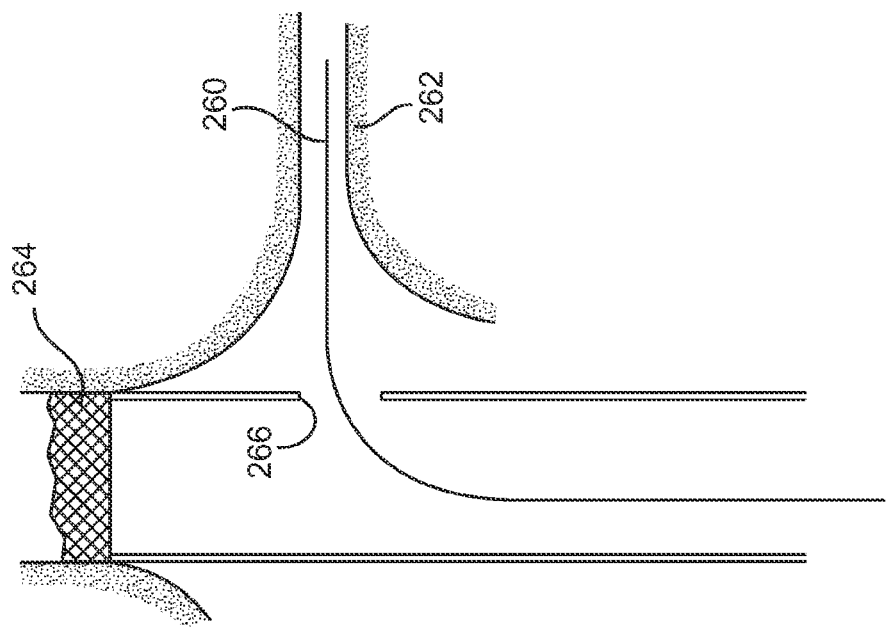

As can be seen in FIG. 16A a main vessel endovascular device 264 has been placed across an aneurysm. The endovascular device 264 includes a side branch opening 266 through which a guidewire 260 is threaded into the lumen contained by the branch vessel wall 262. The balloon expandable branch graft stent system 120 is advanced over the guidewire 260 as seen FIGS. 16B, 16C, and on into through the branch vessel while continuing to follow the track provided by the guidewire 260 into a position where the radiopaque images of the distal ring (hoop) stop 150 and proximal (hoop) stop 152 straddle the opening 266 (marked by radiopaque markers or some other radiopaque visible marking scheme).

Figure 15D:
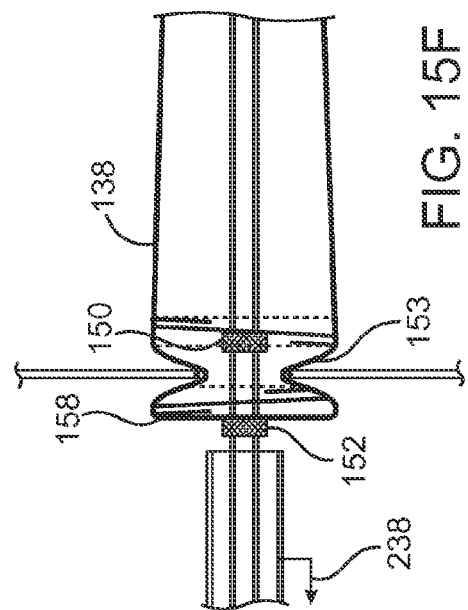
Figure 15F:
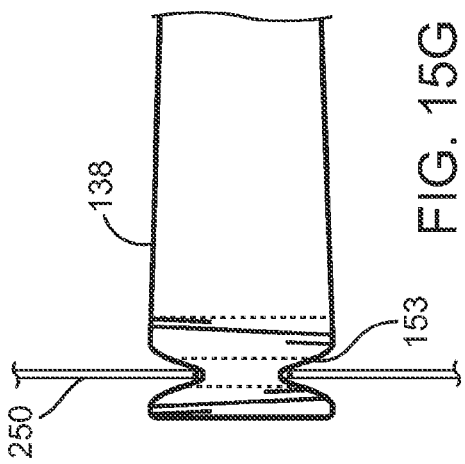
Figure 15E:
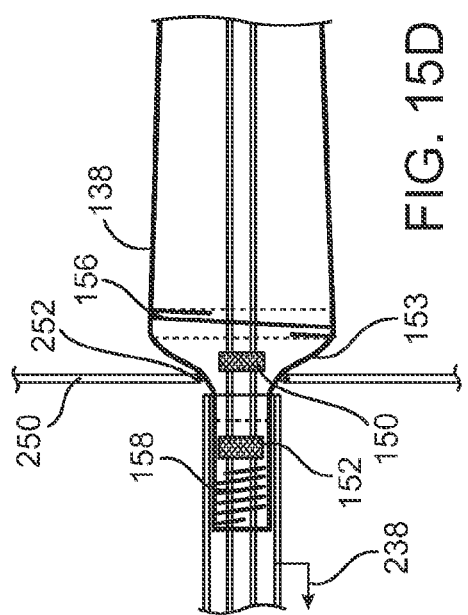
Figure 15G:
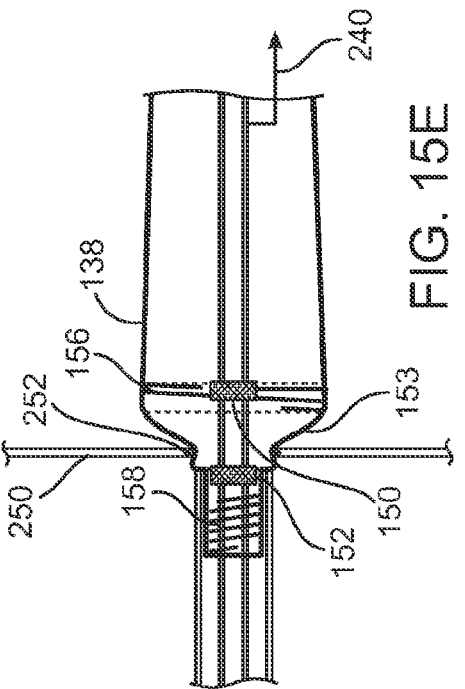
Figure 16C:
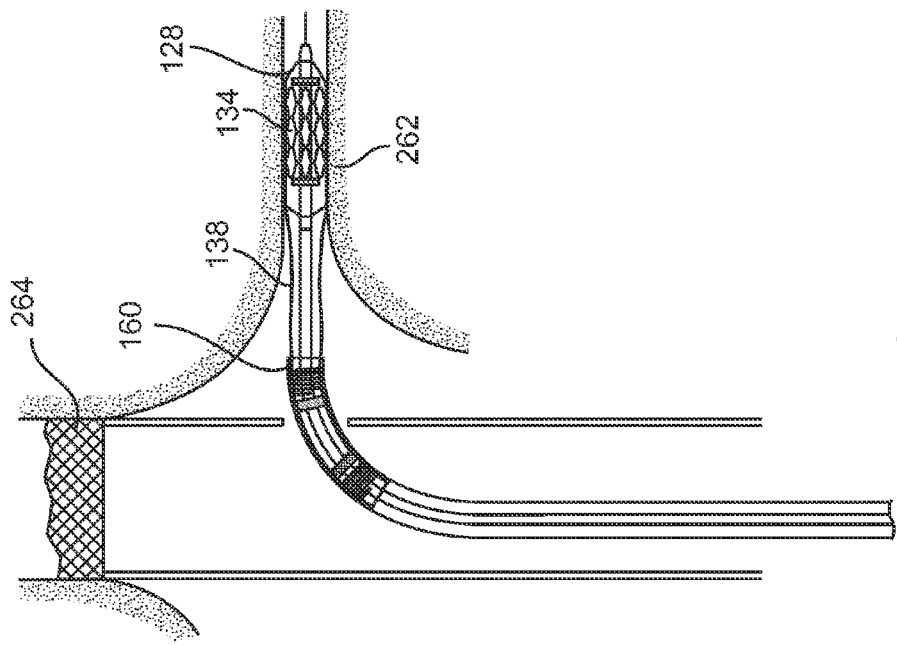
Figure 16D:
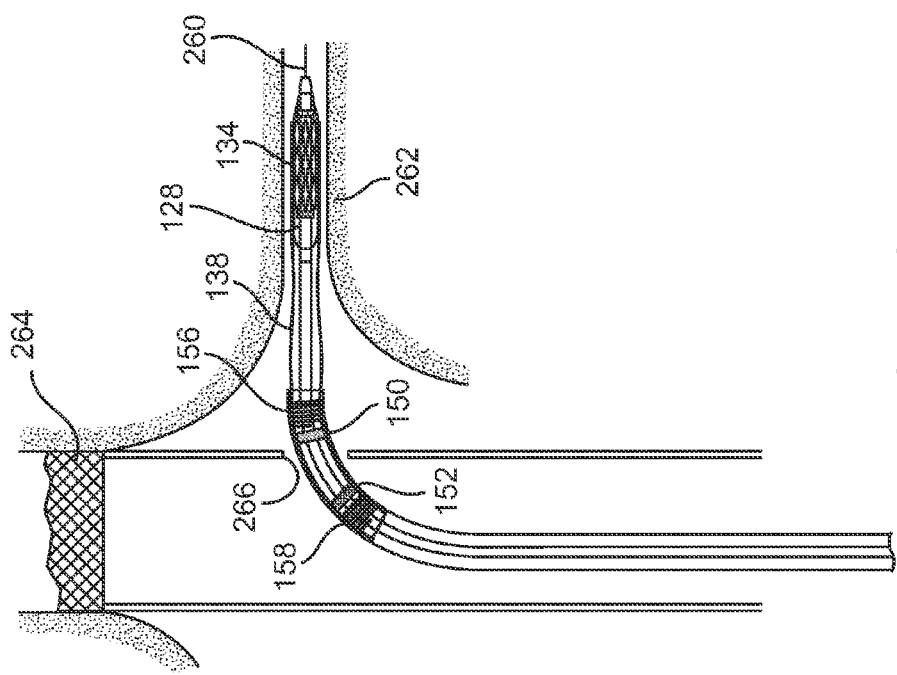
Figure 16G:
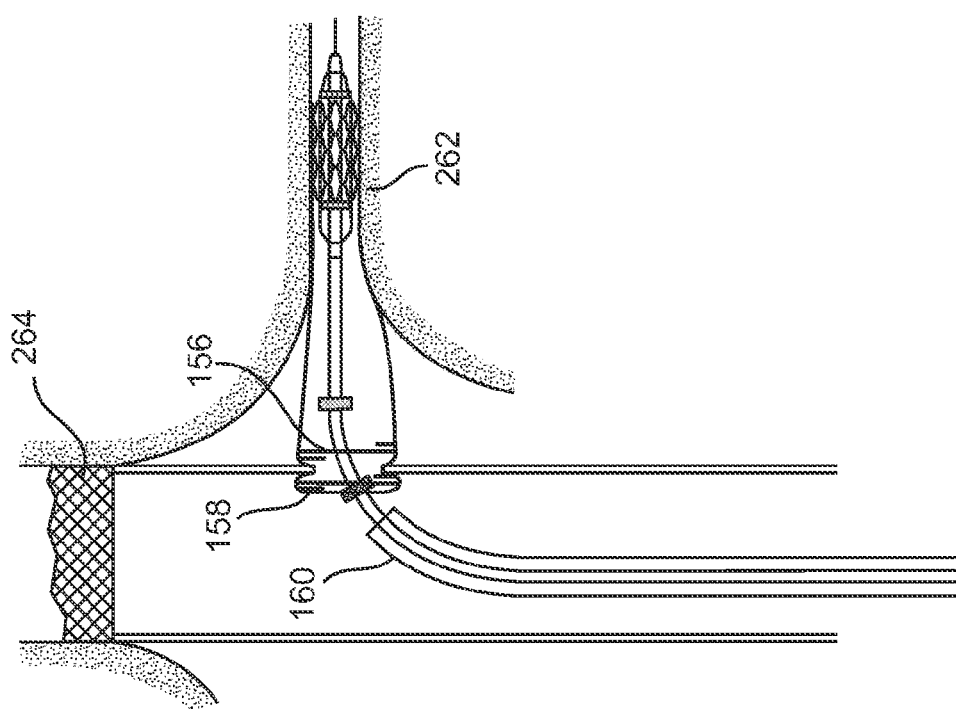
Figure 17:
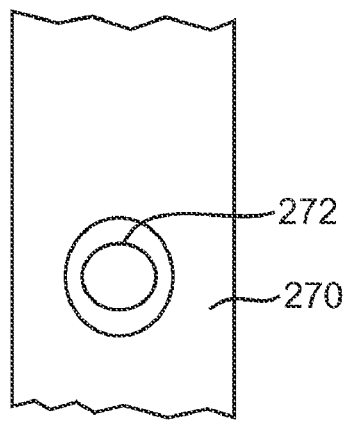
FIG. 17 is a side plan view of a main tubular graft having a side branch opening (fenestration) therein.

The branch graft stent system 120 extending into the branch vessel has graft material 138 and a stent 134 compressed on a balloon 128 (FIG. 16C). Once in position (according to the ring stops 150, 152 discussed above) the balloon 128 is inflated such that the bonded section 136 of the graft material sewn or bonded to the outside of the stent 134 comes into engagement with the branch vessel wall 262 (FIGS. 15A, 16D). The outer sheath 160 is retracted in a direction shown by the arrow 238 so that as the open distal end of the sheath 160 moves closer to the compressed location of the distal coiled nitinol hoop 156 and distal ring (hoop) stop 150 (FIG. 15B). As the outer sheath 160 is further retracted, the distal coiled nitinol hoop 156 is allowed to expand to its unconstrained diameter configuration and is no longer axially constrained by distal ring hoop stop 150 which remains fixed to the catheter outer member (FIGS. 15C, 16E). Once the distal hoop is expanded it may be necessary to move the central members of the catheter assembly forward (or distally) so that the proximal ring stop 152 is brought into close proximity to the location of the main vessel stent graft wall 250 opening 266 having a hoop, grommet, or radiopaque marker 252 so that when the proximal end of the stent graft system is deployed in engagement with or sealing with the main vessel stent graft wall, the sealing engagement can take place without kinking or a rolling of the main and branch graft materials as ring expansion and opening containing forces equalize at their point of contact. (Once repositioning of the catheter to improve proximal alignment has occurred, the distal balloon may be expanded, if necessary, to maintain position of the catheter during the next step). The central inner and outer members 122, 144 can be moved in a direction shown by arrow 240, 244 (FIGS. 15E, 16F. respectively) once the proximal ring stop 152 is in position (close to, but inside the main vessel branch opening marked by marker 252) the outer sheath 160 can be further retracted as shown by the arrow 238 to release the proximal coiled nitinol hoop 158 from the outer sheath 182 and the axial constraints of the proximal ring hoop stop 152. (FIGS. 15F, 16G). Once the branch graft system has been deployed the delivery catheter and guidewire can be removed to leave the branch graft material 138 in a sealing engagement at a ring receiving pocket separation section (sealing section) 153 with the main vessel stent graft wall 250.

The sequence for providing a branch graft stent system includes placing a guidewire through a main vessel stent graft side opening or fenestration, tracking a delivery catheter containing the stent graft branch device into position, deploying the stent at the distal end of the device, retracting the sheath to initially release the distally located hoop or stent, repositioning the catheter to promote the release of the proximal or hoop sealing stent at the correct location, retracting the catheter to release the proximal hoop, and removing the device. An inflatable balloon may or may not be used to re expand the stent or sealing portion in a both balloon expandable and self expanding branch stent graft catheter system. Balloon can also be used to expand stent graft opening 250 after branch vessel graft delivery. Note: Balloon can also be used to expand stent graft opening 250 after branch vessel graft delivery.

Figure 18:
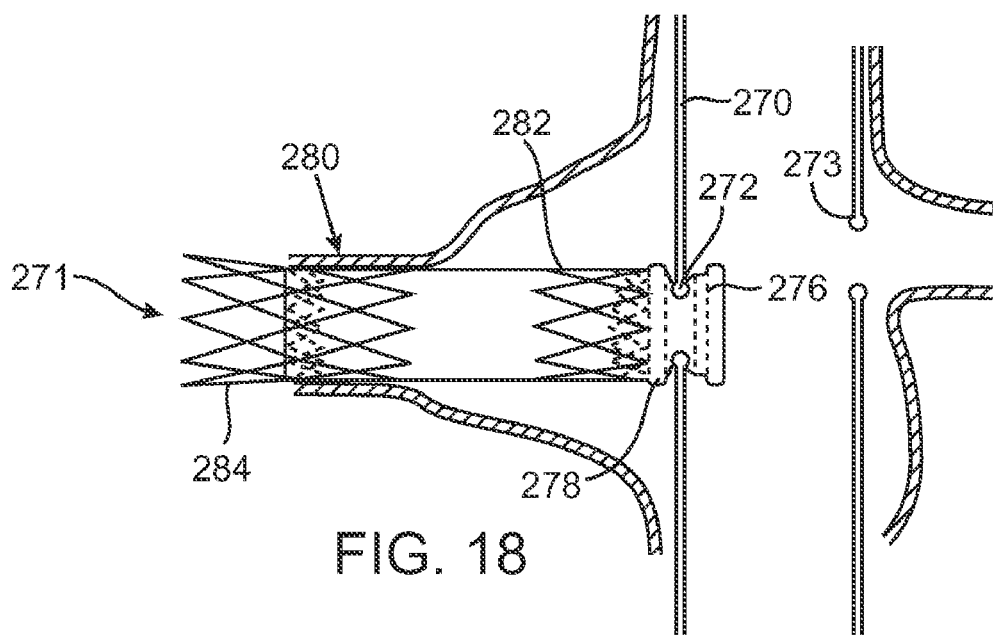
FIG. 18 is a schematic cross sectional view showing one configuration of a side branch graft connected with a tubular main graft.

Referring now to FIGS. 17, 18, 19, and 20, a primary graft 270 is disposed in a primary vessel and has a branch graft opening or port 272 constructed of an insert molded (combination molded) silicone ring that includes enhanced radiopacity by use of known flexible radiopaque materials. The branch graft assembly 271 can be constructed of a tubular graft material with a proximal support spring (stent) 282 and a distal spring (stent) 284 which in an expanded configuration engages the walls of the renal artery 280. The details of the connection feature between the branch graft assembly 271 and the primary graft 270 include structures, as discussed above, including a proximal ring structure 276 and distal ring structure 278 (FIG. 18).

Figure 19:
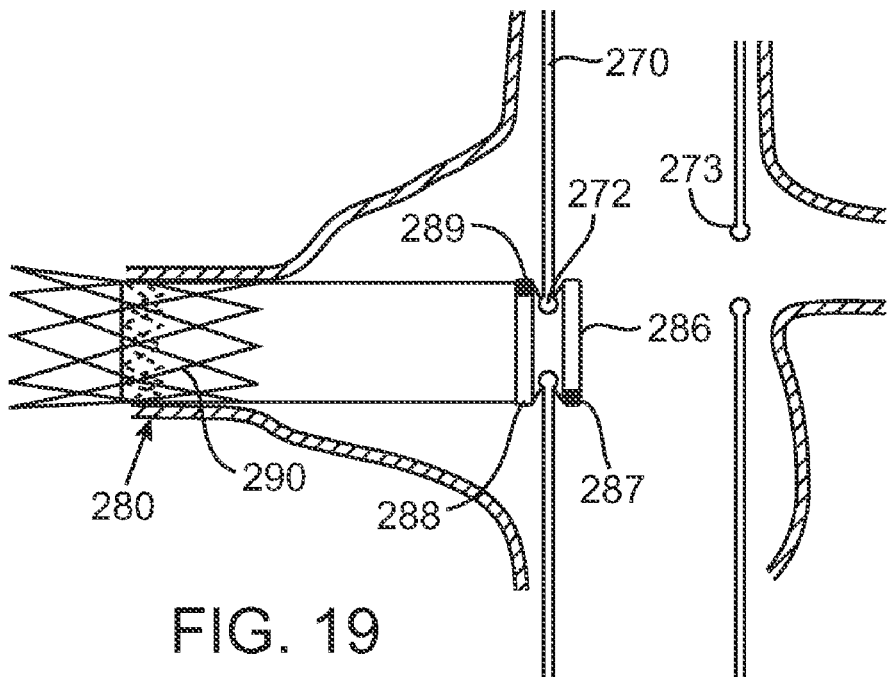
FIG. 19 is a schematic cross sectional view showing another configuration of a tubular branch graft connected to a tubular main graft.

FIG. 19 is an alternate configuration of a branch graft assembly having only a distal spring (stent) 290 engaged with the renal artery 280. The proximal ring structure 286 may include a (radiopaque) marker band or portion 287. Similarly, a distal ring structure 288 may include a marker band or portion 289.

Figure 20:
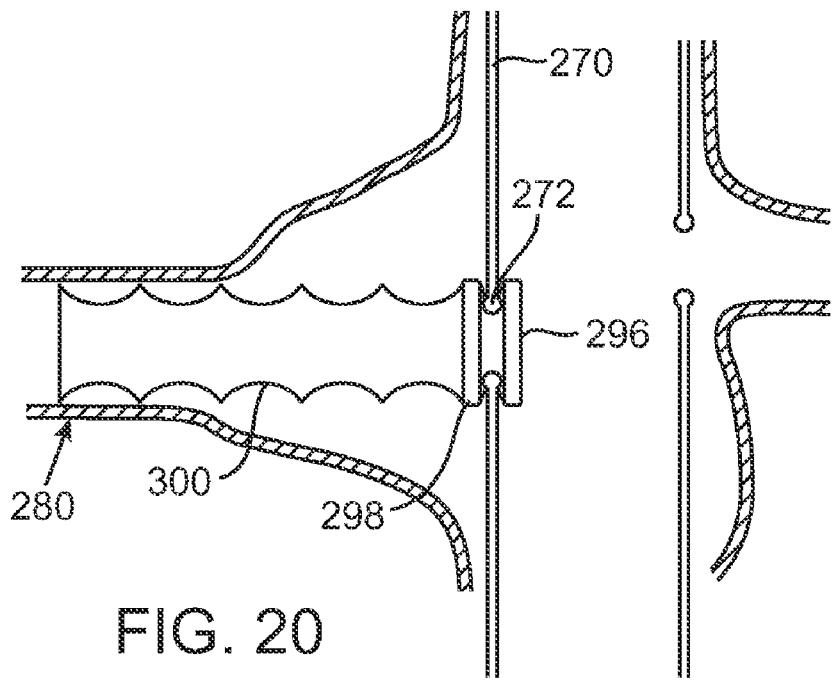
FIG. 20 is a schematic cross sectional view showing another configuration of a tubular branch graft connected to tubular main graft.

FIG. 20 shows an alternate configuration of a branch graft assembly where the branch is constructed of flexible and/or reinforced material having a threaded or ring like or accordion like elements or crimps to span the aneurysmal sac and seal to the inner walls to the renal artery 280. The branch graft assembly of FIG. 20 includes a proximal ring structure 296 and a distal ring structure 298 constructed as described in detail above for the balloon expandable and self expanding assemblies.

The description above is intended by way of example only and is not intended to limit the spirit and scope of the invention or its equivalent as understood by persons skilled in the art.

The invention claimed is:

1. A branch graft delivery system comprising:
a branch graft disposed on a delivery catheter, said delivery catheter having a sheath surrounding a seal portion of said branch graft;
wherein said seal portion of said branch graft includes a first circumferential graft pocket having a first self expanding support ring contained therein and a second circumferential graft pocket having a second self expanding support ring contained therein, wherein said first circumferential graft pocket and said second circumferential graft pocket circumferentially encircle a graft material of said branch graft at first and second locations, respectively, wherein said first and second locations are spaced from each other by a cylindrical channel seal forming section of said graft material, wherein an outer member of said delivery catheter includes a first ring stop and a second ring stop which extend radially outward from said outer member to a diameter slightly less than an inner diameter of said sheath providing annular spaces between each of said ring stops and said sheath, such that said annular spaces are enough to provide clearance for the thickness of said graft material to fit through said annular spaces, while preventing said first and second self expanding support rings from passing through said annular spaces, said graft material being carried in said annular spaces, wherein when said sheath is positioned to surround said first ring stop, said first self expanding support ring is prevented from moving towards said second self expanding support ring and when said sheath is positioned to surround said second ring stop, said second self expanding support ring is prevented from moving towards said first self expanding support ring.

2. The branch graft delivery system of claim 1 wherein said first self expanding support ring and said second self expanding support ring are radially constrained by said sheath.

3. The branch graft delivery system of claim 2 wherein said first self expanding support ring and said second self expanding support ring are exposed by retracting said sheath.

4. The branch graft delivery system of claim 3 wherein said first self expanding support ring and said second self expanding support ring self expand upon being exposed.

5. The branch graft delivery system of claim 1 wherein said first self expanding support ring is axially constrained by said first ring stop.

6. The branch graft delivery system of claim 5 wherein upon retracting said sheath, said first self expanding support ring is no longer axially constrained by said first ring stop.

7. The branch graft delivery system of claim 5 wherein said second self expanding support ring is axially constrained by said second ring stop.

8. The branch graft delivery system of claim 7 wherein upon retracting said sheath, said first and second self expanding support rings are no longer axially constrained by said first and second ring stops.

9. The branch graft delivery system of claim 1 wherein said second self expanding support ring is axially constrained by said second ring stop.

10. The branch graft delivery system of claim 9 wherein upon retracting said sheath, said second self expanding support ring is no longer axially constrained by said second ring stop.

11. The branch graft delivery system of claim 1 wherein said first ring stop and said second ring stop are fixed to said outer member.

12. The branch graft delivery system of claim 1 wherein a balloon is bonded to said outer member.

13. The branch graft delivery system of claim 12 wherein said branch graft further comprises a stent compressed around said balloon, said balloon being expanded to expand said stent.

14. The branch graft delivery system of claim 12 wherein said balloon is further bonded to an inner member, said outer member and said inner member defining a coaxial annular lumen therebetween.

15. The branch graft delivery system of claim 1 wherein said branch graft delivery system is used to deploy said branch graft within a substantially flush branch vessel port of a main stent-graft.

16. The branch graft delivery system of claim 15 wherein said branch graft further comprises a stent, said branch graft delivery system further comprising a balloon around which said stent is located.

17. The branch graft delivery system of claim 15 wherein said sheath is retractable to expose said first self expanding support ring, wherein upon being exposed, said first self expanding support ring is capable of self expanding to engage a first side of said branch vessel port.

18. The branch graft delivery system of claim 17 wherein said sheath is further retractable to expose said second self expanding support ring, wherein upon being exposed, said second self expanding support ring is capable of self expanding to engage a second side of said branch vessel port.

19. The branch graft delivery system of claim 18 wherein a radiopaque image of said first ring stop on said first side of said branch vessel port and a radiopaque image of said second ring stop on said second side of said branch vessel port are capable of being used to position said branch graft in said branch vessel port.

20. The branch graft delivery system of claim 1 wherein said branch graft further comprises:
a first pocket material sewn to said graft material at a first pocket proximal pocket seam and a first pocket distal pocket seam to define said first circumferential graft pocket; and
a second pocket material sewn to said graft material at a second pocket proximal pocket seam and a second pocket distal pocket seam to define said second circumferential graft pocket.

\* \* \* \* \*